United States Patent [19]

Leuenberger et al.

[11] Patent Number: 4,734,367

[45] Date of Patent: Mar. 29, 1988

[54] PROCESS TO PRODUCE ALPHA-SUBSTITUTED DERIVATIVES OF 3-HYDROXYPROPIONIC ACID

[75] Inventors: Hans G. W. Leuenberger, Bättwil; Peter K. Matzinger, Rodersdorf; Dieter Seebach; Max F. Züger, both of Zurich, all of Switzerland

[73] Assignee: Hoffmann-La Roche Inc., Nutley, N.J.

[21] Appl. No.: 674,207

[22] Filed: Nov. 23, 1984

[30] Foreign Application Priority Data

Dec. 6, 1983 [CH] Switzerland ............... 6510/83

[51] Int. Cl.$^4$ ............................................. C12P 7/62
[52] U.S. Cl. .................................... 435/135; 435/136; 435/146; 435/253; 435/872; 435/897; 435/904; 435/913; 435/921; 435/932; 435/936; 435/942; 435/944
[58] Field of Search ............... 435/135, 136, 146, 253, 435/822, 872, 897, 904, 913, 921, 932, 936, 942, 944; 435/886, 911

[56] References Cited

U.S. PATENT DOCUMENTS 4,326,031  4/1982  Wandry ............... 435/146

FOREIGN PATENT DOCUMENTS 0155094  9/1983  Japan ............... 435/135
2132614  7/1984  United Kingdom .

OTHER PUBLICATIONS

Patent Abstracts of Japan, 6:139, C-116, 1017, (7-28-1982).
Patent Abstracts of Japan, 7:277, C-199, 1422 (12-9-1983).
Patent Abstracts of Japan, 6:110, C-109, 988 (6-22-82).
Chemical Abstract 100:84198q (vol. 100, p. 428) 1984.
Zuger et al., "Preparation of Ethyl-(R)-(−)-3-Hydroxy-2-Methyl-Propanoate by Yeast Reduction of Ethyl α-Formylpropanoate", *Angew Chem Int. Ed. Engl.*, 22(12):1012, Dec. 1, 1983.

Primary Examiner—Margaret Moskowitz
Attorney, Agent, or Firm—Jon S. Saxe; Bernard S. Leon; Richard J. Mazza

[57] ABSTRACT

The manufacture of optically active compounds of the formula

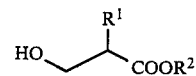

I wherein $R^1$ signifies alkyl, phenyl or benzyl and $R^2$ signifies hydrogen or a customary ester residue, by the fermentative reduction of compounds of the formula

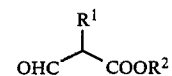

II wherein $R^1$ and $R^2$ have the above significance.

The compounds obtained are valuable intermediates in organic syntheses.

9 Claims, No Drawings

PROCESS TO PRODUCE ALPHA-SUBSTITUTED DERIVATIVES OF 3-HYDROXYPROPIONIC ACID

DESCRIPTION OF THE INVENTION

The invention is concerned with a microbiological process for the manufacture of optically active, α-substituted derivatives of 3-hydroxypropionic acid. The compounds obtainable in accordance with the invention are valuable intermediates in organic syntheses and can be used, for example, for the manufacture of α-tocopherol, muscones, pharmaceuticals, insecticides, agents which induce fruit fall and the like.

The process in accordance with the invention comprises manufacturing optically active 3-hydroxypropionic acid derivatives of the general formula

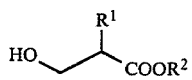    I wherein $R^1$ is alkyl, phenyl or benzyl and $R^2$ is hydrogen or a customary ester residue,
by fermentatively reducing a compound of the general formula

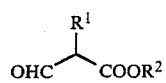    II wherein $R^1$ and $R^2$ are as above.

The term "alkyl" used in connection with $R^1$ embraces preferably straight-chain or branched alkyl groups with 1 to 6 carbon atoms, such as methyl, ethyl, propyl, isopropyl, butyl and the like. Especially preferred residues $R^1$ are phenyl and particularly methyl. In the latter two cases formula I corresponds to tropic acid and 3-hydroxyisobutyric acid or their esters.

The term "customary ester residue" embraces the residues which are usually present in carboxylic acid esters, such as alkyl, aryl, aralkyl, alkylaryl and the like, for example methyl, ethyl, isopropyl, t-butyl, phenyl, benzyl and tolyl. $R^2$ in formulae I and II above preferably signifies hydrogen, $C_1$–$C_6$-alkyl, phenyl or benzyl, especially methyl, ethyl or t-butyl.

The process in accordance with the invention opens up a novel advantageous route for the manufacture of optically active compounds of formula I. The good yields observed with the use of racemic starting materials of formula II indicates that the reduction in accordance with the invention proceeds entirely or at least to a large extent via the enol form of the compounds of formula II and therefore the configuration of the product of formula I is not influenced or is influenced only insignificantly by the configuration of the starting material of formula II.

The process in accordance with the invention is conveniently carried out by cultivating a microorganism producing the compounds of formula I in an aqueous nutrient medium in the presence of a compound of formula II or continuing the incubation after the cultivation in the presence of a compound of formula II.

Depending on the microorganism used there is formed predominantly the (R)- or (S)-form of the compounds of formula I. Suitable microorganisms producing the compounds of formula I can be found readily by testing arbitrary microorganisms—preferably aerobic or facultative aerobic yeasts, fungi or bacteria—on the educt of formula II used in accordance with the invention. The process in accordance with the invention is preferably used for the manufacture of the (R)-form of the compounds of formula I.

Examples of preferred microorganisms which can be used are:

1. Procaryotes
   1.1. Bacteria of the genus:
       Pseudomonas
           such as *Pseudomonas aeruginosa* (e.g. NRRL B771)
           such as *Pseudomonas aurofaciens* (e.g. ATCC 13985)
           such as *Pseudomonas denitrificans* (e.g. NRRL B1028)
           such as *Pseudomonas fluorescens* (e.g. ATCC 13430)
           such as *Pseudomonas oleovorans* (e.g. ATCC 8062)
           such as *Pseudomonas piscicida* (e.g. ATCC 15251)
           such as *Pseudomonas putida* (e.g. ATCC 21244)
           such as *Pseudomonas rubescens* (e.g. ATCC 12099)
           such as *Pseudomonas saccharophila* (e.g. ATCC 15946)
           such as *Pseudomonas testosteroni* (e.g. ATCC 11996)
   1.2. Mycelium-forming bacteria (Actinomycetes) of the genus:
       Nocardia
           such as *Nocardia asteroides* (e.g. IMRU 833)
           such as *Nocardia brasiliensis* (e.g. IMRU 536)
           such as *Nocardia opaca* (e.g. CBS 26639)
       Streptomyces
           such as *Streptomyces aureus* (e.g. ATCC 9309)
           such as *Streptomyces clavuligerus* (e.g. NRRL 3585)
           such as *Streptomyces eurocidicus* (e.g. NRRL B1676)
           such as *Streptomyces fradiae* (e.g. NRRL B1195)
           such as *Streptomyces flavochromogenans* (e.g. CBS 74472)
           such as *Streptomyces griseus* (e.g. IMRU 3570, NRRL 15727)
           such as *Streptomyces hirsutus* (e.g. ETH 16281)
           such as *Streptomyces hydrogenans* (e.g. ATCC 19631)
           such as *Streptomyces mediocidicus* (e.g. ATCC 13278)
           such as *Streptomyces olivaceus* (e.g. NRRL B-1125)
           such as *Streptomyces rimosus* (e.g. ATCC 10970)
           such as *Streptomyces roseochromogenus* (e.g. ATCC 13400)
           such as Streptomyces sp. (ETH 19121, NRRL 15728)
           such as *Streptomyces viridochromogenes* (e.g. NRRL B1511)
2. Eucaryotes:
   2.1. Fungi of the genus:
       Aspergillus
           such as *Aspergillus niger* (e.g. ATCC 11394)
           such as *Aspergillus ochraceus* (e.g. NRRL 398)
       Byssochlamis
           such as *Byssochlamis fulva* (e.g. NRRL 3493)
       Curvularia
           such as *Curvularia lunata* (e.g. NRRL 2380)
       Fusarium
           such as *Fusarium solani* (e.g. ATCC 12823)
       Geotrichum
           such as *Geotrichum candidum* (e.g. CBS 23376)
       Gibberella
           such as *Gibberella baccata* (e.g. ATCC 11857)
           such as *Gibberella fujikuroi* (e.g. ATCC 14842)
       Gliocladium
           such as *Gliocladium roseum* (e.g. NRRL 8194)
       Mucor
           such as *Mucor circinelloides* (e.g. ETH 2605)
       Paecilomyces
           such as *Paecilomyces carneus* (e.g. NRRL 11054)
       Penicillium
           such as *Penicillium brevi-compactum* (e.g. ATCC 32005)
           such as *Penicillium citrinum* (e.g. ATCC 9849)
           such as *Penicillium lilacinum* (e.g. ATCC 10114)
           such as *Penicillium notatum* (e.g. NRRL 832)
           such as *Penicillium purpurogenum* (e.g. NRRL 1059)
   2.2. Yeasts of the genus:
       Candida
           such as *Candida albicans* (e.g. ATCC 18804)
           such as *Candida parapsilosis* (e.g. CBS 1954)
           such as *Candida humicola* (e.g. NRRL Y-1266)
           such as *Candida tropicalis* (e.g. ATCC 9968)

-continued

Cryptococcus
such as *Cryptococcus laurentii* (e.g. IFO 0609)
Rhodosporidium
such as *Rhodosporidium toruloides* (e.g. ATCC 10657)
Rhodotorula
such as *Rhodotorula rubra* (e.g. IFO 0714)
such as *Rhodotorula glutinis* (e.g. NRRL Y-15726)
Saccharomyces
such as *Saccharomyces cerevisiae* (e.g. ATCC 7754)
such as *Saccharomyces rouxii* (e.g. CBS 710)
Schizosaccharomyces
such as *Schizosaccharomyces pombe* (e.g. CBS 1058)
Torulopsis
such as *Torulopsis aeria*
such as *Torulopsis magnoliae* (e.g. NRRL Y-2024)
such as *Torulopsis rotundata* (e.g. NRRL 41402)

The data given above in parentheses relates in each case to the corresponding strains which have been deposited with one of the following culture collections under the number given:
NRRL=Northern Utilization Research and Development Division of U.S.D.A., Peoria, Ill., USA
ATCC=American Type Culture Collection, Rockville, Md., USA
CBS=Centraal-Bureau voor Schimmelcultures, Baarn, Holland
ETH=Eidgenössische Technische Hochschule, Zurich, Switzerland
IFO=Institute for Fermentation, 54-4 Juso Nishinomachi, Higashiyodogawaku, Osaka, Japan
IMRU=Institute of Microbiology, Rutgers-The State University, New Brunswick, N.J., USA.

Microorganisms which yield the desired product of formula I in an optical purity of at least about 90% ee are preferably used. Preferred microorganisms which can be used in the process in accordance with the invention are mycelium-forming bacteria and yeasts, especially microorganisms of the genera Nocardia and Streptomyces or Candida, Rhodotorula and Torulopsis. Especially preferred are microorganisms of the species *Streptomyces roseochromogenus, Candida humicola, Streptomyces hydrogenans, Streptomyces griseus*, Streptomyces sp. and *Rhodotorula glutinis*, especially the deposited strains referred to above and mutants thereof. In order to ensure their viability, strains of the three last-named species were newly deposited on Nov. 30, 1983 at NRRRL under the numbers 15727, 15728 and Y-15726.

It will be appreciated that each of the microorganisms used in accordance with the invention should be cultivated before use in the fermentation in accordance with the invention. The cultivation is generally carried out in a manner known per se in an aqueous medium with the aid of the usual nutrient materials, i.e. in the presence of a carbon source (e.g. glucose, fructose, saccharose, maltose and/or malt extract), a nitrogen source (e.g. urea, peptone, yeast extract, meat extract, amino acids and/or ammonium salts) and optionally inorganic salts (e.g. magnesium, sodium, potassium, calcium and/or ferrous salts) and other growth-promoting substances (e.g. vitamins).

The cultivation medium with the microorganism growing therein can generally be used directly for the reduction in accordance with the invention. After the addition of the educt of formula II the fermentation can then be carried out without further additives.

The composition of the fermentation medium used in accordance with the invention can, however, also be substantially simpler and can consist, for example, solely of a solution of the educt of formula II and the microorganism used. However, it is advantageous to add to the aqueous medium an assimilable carbon source (for example in the form of a sugar such as glucose, fructose, saccharose, maltose and the like) as a nutrient for the microorganism in order that the viability of the microorganism and the metabolic activity associated therewith remains as long as possible. The carbon source is preferably added in an amount of about 10-100 g/l. In the case of long fermentation times it is advantageous to add the carbon source in a preferred amount of 10-100 g/l once or several times.

The addition of a nitrogen source to the fermentation medium is not necessary. However, if desired, an assimilable nitrogen source (for example in the form of urea, peptone, yeast extract, meat extract, amino acids, ammonium salts and the like) can be added, preferably in an amount of about 1-50 g/l. The fermentation medium can also contain inorganic salts such as magnesium, sodium, potassium, calcium and/or ferrous salts and other growth-promoting substances such as vitamins and the like.

The pH-value of the fermention medium should preferably lie within the range of 2 to 10, especially 3 to 8, a range which can be achieved in most cases without particular additives. If desired, the pH-value can be adjusted by using buffers, acids or bases, e.g. phosphate, phthalate or Tris buffers [tris-(hydroxymethyl)-aminomethane], hydrochloric acid, sodium hydroxide and the like. The temperature can vary in wide limits, e.g. between 10° C. and 40° C., preferably between 20° C. to 35° C.

In order to obtain optimum yields it is advantageous to incorporate the educt of formula II in the fermentation broth in a concentration of about 0.05-5.0 wt.%, especially about 0.1-0.5 wt.%. After the reaction has been carried out educt in a preferred concentration of about 0.1-0.5 wt.% can again be added. This procedure can be repeated until the microorganisms become inactivated. The substrate can also be added continuously with the aid of a pump.

The advantageous fermentation time depends on the microorganisms used. In the case of a single addition of educt it generally lies between about 2 and 100 hours, especially between 4 and 24 hours. Shorter fermentation times are, however, frequently sufficient. In the case of repeated or continuous addition of educt the fermentation time can be correspondingly lengthened.

The fermentation is preferably carried out aerobically, for example while stirring, shaking with the admission of air or by means of an aeration apparatus. The usual anti-foaming agents such as silicon oils, polyalkylene glycol derivatives, soya bean oil and the like can be added in order to control foaming. A microorganism which is in the non-growing (stationary) phase is preferably used. The choice of a stationary microorganism has the advantage that the biotransformation need not be carried out under sterile conditions insofar as there is used a nutrient medium which permits no substantial reproduction of microorganisms, for example a nutrient medium without a nitrogen source.

After completion of the reaction the fermentation product can be isolated from the fermentation broth in the usual manner. The isolation is preferably carried out by extraction with an organic solvent which is not soluble in water, for example with an aliphatic or cycloaliphatic, optionally chlorinated hydrocarbon, an aliphatic ester or an aliphatic ether, such as hexane, cyclohexane, methylene chloride, chloroform, carbon tetrachloride, ethyl acetate, butyl acetate, amyl acetate, diethyl ether, diisopropyl ether and the like. Ethyl acetate is a preferred solvent.

If desired, the crude product obtained can be purified in the usual manner, for example by distillation, crystallization, chromatographic methods etc. In many cases it is advantageous to convert the crude product previously into a suitable derivative, for example by esterification of the hydroxy group with 3,5-dinitrobenzoyl chloride, a chloride of an optically active carboxylic acid such as α-methoxy-α-trifluoromethyl-phenylacetyl chloride, and the like, or by carbamate formation, for example with optically active α-naphthyl-ethyl isocyanate.

The starting materials of formula II are known or are analogues of known compounds. They can be obtained, for example, starting from the corresponding carboxylic acids or their esters according to known formylation reactions (e.g. with lithium diisopropylamide and ethyl formate).

Since the compounds of formula I have a "pseudo-sym-metric" chiral structure [Helv. Chim. Acta 60, 925 (1977)], starting from one antipode of the compounds of formula I there are accessible by purely chemical steps each of the two antipodal forms of further key compounds for organic syntheses. Such reactions and further possible applications for the compounds manufactured in accordance with the invention are described in detail in Helv. Chim. Acta. 60, 925 (1977) and 64, 1158 (1981); J. Org. Chem. 41, 3505 (1976); Tetrahedron Lett. 22, 3925 (1981) and 31, 2745 (1978); Tetrahedron 37, 3873 (1981); J. Amer. Chem. Soc. 101, 6789 (1979), 102, 2117-21 (1980), 104, 4496 (1982) and 104, 5528 (1982) and in British Patent Publication No. 1229259. Further, by chain-lengthening using known C—C linkage methods (e.g. Wittigor Grignard reactions) there are accessible insecticides such as, for example, the insecticides described in Chemtech 1976, 358. The above and below-mentioned prior art disclosures are incorporated herein by reference.

The process in accordance with the invention is illustrated in more detail by the following Examples. The educts were used in racemic form in each case. The products obtained in Examples 1-7 and 10-12 were each esterified with α-methoxy-α-trifluoromethyl-phenylacetyl chloride [J. Org. Chem. 34, 2543 (1969)] and the products obtained in Examples 8, 9 and 14 were each converted into the carbamate with (S)-(+)-α-naphthylethyl isocyanate [e.g. J. Org. Chem. 39, 3904 (1974)] and subsequently the optical purity of the products was determined on the basis of the NMR spectra and gas chromatograms of these esters or carbamates.

EXAMPLE 1

The yeast *Candida humicola* NRRL Y-1266 was cultivated on an agar slant with 7.5 ml of medium 1 consisting of 1 wt.% of yeast extract, 1 wt.% of peptone, 2 wt.% of glucose, 1.6 wt.% of agar and 94.4 wt.% of distilled water. After incubation at 30° C. for 3 days the batch was treated with 9 ml of 0.9% (wt./vol.) sodium chloride solution and the cells were suspended. Subsequently, a shaking flask containing 100 ml of medium 1 without the addition of agar (i.e. a medium consisting of 1 wt.% of yeast extract, 1 wt.% of peptone, 2 wt.% of glucose and 96 wt.% of distilled water) was inoculated with 1 ml of the suspension obtained. After an incubation period of 3 days while shaking at 30° C. the cells were centrifuged off and suspended in 100 ml of 5% (wt./vol.) of glucose solution. The suspension obtained was treated with 0.1 g of ethyl α-formylpropionate and incubated further at 30° C. while shaking. After 5 hours the batch was extracted with ethyl acetate, there being obtained ethyl (R)-(−)-3-hydroxy-isobutyrate in an optical purity of 95.2% ee.

EXAMPLE 2

The yeast *Rhodotorula glutinis* NRRL Y-15726 was cultivated on an agar slant with 7.5 ml of medium 1 consisting of 1 wt.% of yeast extract, 1 wt.% of peptone, 2 wt.% of glucose, 1.6 wt.% of agar and 94.4 wt.% of distilled water. After incubation at 30° C. for 3 days the batch was treated with 9 ml of 0.9% (wt./vol.) sodium chloride solution and the cells were suspended. Subsequently, a shaking flask containing 100 ml of medium 1 without the addition of agar (i.e. a medium consisting of 1 wt.% of yeast extract, 1 wt.% of peptone, 2 wt.% of glucose and 96 wt.% of distilled water) was inoculated with 1 ml of the suspension obtained. After an incubation period of 24 hours while shaking at 30° C. the pre-culture was treated with 0.1 g of ethyl α-formylpropionate and incubated further at 30° C. while shaking. After 24 hours the batch was extracted with ethyl acetate, there being obtained ethyl (R)-(−)-3-hydroxy-isobutyrate in an optical purity of 96.8% ee.

EXAMPLE 3

*Streptomyces roseochromogenus* ATCC 13400 was cultivated on an agar slant with 7.5 ml of medium 2 which consisted of 0.4 wt.% of yeast extract, 1 wt.% of malt extract, 0.4 wt.% of saccharose, 1.5 wt.% of agar and 96.7 wt.% of tap water and which had been adjusted with sodium hydroxide to a pH-value of 7.3. After incubation at 30° C. for 6 days the batch was treated with 9 ml of 0.9% (wt./vol.) Sodium chloride solution. Subsequently, 100 ml of medium 3 consisting of 1 wt.% of cornsteep, 1 wt.% of soya meal, 1 wt.% of glucose and 97 wt.% of distilled water were inoculated with 1 ml of the spore suspension obtained. After an incubation period of 3 days dwhile shaking at 30° C. 0.1 g of ethyl α-formylpropionate was added directly to the pre-culture and incubated further while shaking at 30° C. After a reaction time of 4 hours the batch was extracted with ethyl acetate, there being obtained ethyl (R)-(−)-3-hydroxy-isobutyrate in an optical purity of 89.8% ee.

EXAMPLE 4

*Streptomyces griseus* NRRL 15727 was cultivated on a agar slant with 7.5 ml of medium 2 which consisted of 0.4 wt.% of yeast extract, 1 wt.% of malt extract, 0.4 wt.% of saccharose, 1.5 wt.% of agar and 96.7 wt.% of tap water and which had been adjusted with sodium hydroxide to a pH-value of 7.3. After incubation at 30° C. for 6 days the batch was treated with 9 ml of 0.9% (wt./vol.) sodium chloride solution. Subsequently, 100 ml of medium 4, which consisted of 2 wt.% of glucose, 0.5 wt.% of peptone, 0.5 wt.% of meat extract, 0.3 wt.% of yeast extract, 0.3 wt.% of calcium carbonate and 96.4 wt.% of distilled water and which had been adjusted with sodium hydroxide to a pH-value of 7.0, were inoculated with 1 ml of the spore suspension obtained. After an incubation period of 3 days while shaking at 30° C. 0.1 g of ethyl α-formylbutyrate was added directly to the pre-culture and incubated further while shaking at 30° C. After a reaction time of 24 hours the batch was extracted with ethyl acetate, there being obtained ethyl (R)-(−)-2-(hydroxymethyl)butyrate in an optical purity of 88.4% ee.

EXAMPLE 5

*Streptomyces griseus* NRRL 15727 was cultivated with medium 2 and 4 as described in Example 4. After an incubation period of 3 days while shaking at 30° C. 0.1 g of ethyl α-formylisovalerate was added directly to the pre-culture (medium 4) and incubated further while shaking at 30° C. After a reaction time of 24 hours the batch was extracted with ethyl acetate, there being obtained ethyl (R)-(−)-2-(hydroxymethyl)isovalerate in an optical purity of 93% ee.

EXAMPLE 6

*Streptomyces griseus* NRRL 15727 was cultivated with medium 2 and 4 as described in Example 4. After an incubation period of 3 days while shaking at 30° C. 0.1 g of ethyl α-formyl-α-phenylacetate was added directly to the pre-culture (medium 4) and incubated further while shaking at 30° C. After a reaction time of 4 hours the batch was extracted with ethyl acetate, there being obtained ethyl R-(+)-tropate [ethyl R-(+)-3-hydroxy-2-phenylpropionate] in an optical purity of 95.6% ee.

EXAMPLE 7

*Streptomyces sp.* NRRL 15728 was cultivated with medium 2 and 4 in a manner analogous to that described in Example 4. After an incubation period of 3 days while shaking at 30° C. 0.1 g of ethyl α-formylpropionate was added directly to the pre-culture (medium 4) and incubated further while shaking at 30° C. After a reaction time of 24 hours the batch was extracted with ethyl acetate, there being obtained ethyl (R)-(−)-3-hydroxyisobutyrate in an optical purity of 93.4% ee.

EXAMPLE 8

The yeast *Candida humicola* NRRL Y-1266 was cultivated on an agar slant with 7.5 ml of medium 1 consisting of 1 wt.% of yeast extract, 1 wt.% of peptone, 2 wt.% of glucose, 1.6 wt.% of agar and 94.4 wt.% of distilled water. After incubation at 30° C. for 3 days the batch was treated with 9 ml of 0.9% (wt./vol.) sodium chloride solution and the cells were suspended. Subsequently, a shaking flask containing 100 ml of medium 1 without the addition of agar (i.e. a medium consisting of 1 wt.% of yeast extract, 1 wt.% of peptone, 2 wt.% of glucose and 96 wt.% of distilled water) was inoculated with 1 ml of the suspension obtained. After an incubation period of 24 hours while shaking at 30° C. the pre-culture was treated with 0.1 g of ethyl α-formyl-β-phenylpropionate and incubated further while shaking at 30+ C. After 1 hour the batch was extracted with ethyl acetate, there being isolated ethyl (R)-(+)-2-benzyl-3-hydroxypropionate in an optical purity of 73.6% ee.

EXAMPLE 9

*Penicillium notatum* NRRL 832 was cultivated on an agar slant with 7.5 ml of medium 5 consisting of 2 wt.% of sucrose, 1.5 wt.% of agar and 96.5 wt.% of beer wort (specific gravity 1.05–1.035) having a pH of 6.5. After incubation at 30° C. for 6 days the batch was treated with 9 ml of 0.9% (wt./vol.) sodium chloride solution and the cells were suspended. Subsequently, a shaking flask containing 100 ml of medium 6, which consisted of 1 wt.% of cornsteep, 1 wt.% of soya meal, 1 wt.% of glucose and 97 wt.% of distilled water, was inoculated with 1 ml of the suspension obtained. After an incubation period of 3 days while shaking at 30° C. 0.1 g of ethyl α-formyl-β-phenylpropionate was added directly to the pre-culture and incubated further while shaking at 30° C. After a reaction time of 1 hour the batch was extracted with ethyl acetate, there being obtained ethyl (R)-(+)-2-benzyl-3-hydroxypropionate in an optical purity of 88.5% ee.

EXAMPLE 10

*Paecilomyces carneus* NRRL 11054 was cultivated with medium 5 and 6 as described in Example 9. After an incubation period of 3 days while shaking at 30° C. 0.1 g of ethyl α-formylbutyrate was added directly to the pre-culture and incubated further while shaking at 30° C. After a reaction time of 1 hour the batch was extracted with ethyl acetate, there being obtained ethyl (R)-(−)-2-(hydroxymethyl)butyrate in an optical purity of 86.5% ee.

EXAMPLE 11

*Streptomyces hydrogenans* ATCC 19631 was cultivated with medium 2 and 4 as described in Example 4. After an incubation period of 3 days while shaking at 30° C. 0.1 g of ethyl α-formylisovalerate was added directly to the pre-culture (medium 4) and incubated further while shaking at 30° C. After a reaction time of 24 hours the batch was extracted with ethyl acetate, there being obtained ethyl (R)-(−)-2-(hydroxymethyl)isovalerate in an optical purity of 96.5% ee.

EXAMPLE 12

*Streptomyces hydrogenans* ATCC 19631 was cultivated with medium 2 and 4 as described in Example 4. After an incubation period of 3 days while shaking at 30° C. 0.1 g of ethyl α-formyl-α-phenylacetate was added directly to the pre-culture (medium 4) and incubated further while shaking at 30° C. After a reaction time of 24 hours the batch was extracted with ethyl acetate, there being obtained ethyl R-(+)-tropate [ethyl R-(+)-3-hydroxy-2-phenylpropionate] in an optical purity of 95.5% ee.

EXAMPLE 13

The yeast *Candida albicans* ATCC 18804 was cultivated with medium 1 in a manner analogous to that described in Example 8. After an incubation period of 1 day while shaking at 30° C. 0.1 g of ethyl α-formylbutyrate was added directly to the pre-culture. After a reaction time of 1 hour the batch was extracted with ethyl acetate, there being obtained ethyl (S)-(+)-2-(hydroxymethyl)butyrate in an optical purity of 76% ee (the optical antipode to the compound obtained in Example 4).

EXAMPLE 14

*Streptomyces hydrogenans* ATCC 19631 was cultivated with medium 2 and 4 as described in Example 4. After an incubation period of 3 days while shaking at 30° C. 0.1 g of ethyl α-formyl-β-phenylpropionate was added directly to the pre-culture. After a reaction time of 24 hours the batch was extracted with ethyl acetate, there being obtained ethyl (R)-(+)-2-benzyl-3-hydroxypropionate in an optical purity of 99% ee.

I claim:

1. A process for the manufacture of optically active 3-hydroxypropionic acid derivatives of the general formula

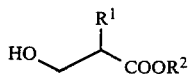 I wherein $R^1$ is selected from the group consisting of alkyl, phenyl and benzyl and $R^2$ is selected from the group consisting of hydrogen, alkyl having from one to six carbon atoms, phenyl and benzyl,
which process comprises fermentatively reducing a compound of the general formula

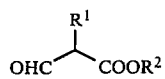 II wherein $R^1$ and $R^2$ are as above.

2. A process according to claim 1, wherein a microorganism producing the compound of formula I is cultivated in an aqueous nutrient medium in the presence of a compound of formula II which is simultaneously fermentatively reduced, or a microogranism producing the compound of formula I is first cultivated in an aqueous nutrient medium in the absence of a compound of formula II and then the incubation is continued in the presence of a compound of formula II which is fermentatively reduced.

3. A process according to claim 1 or 2, wherein the reaction is carried out with a microorganism selected from the genus Nocardia, Streptomyces, candida, Rhodotorula or Torulopsis.

4. A process according to claim 1, wherein the reaction is carried out with a microorganism selected from the species *Nocardia asteroides, Nocardia opaca, Streptomyces flavochromogenans, Streptomyces griseus, Streptomyces hirsutus, Streptomyces hydrogenans, Streptomyces mediocidicus, Streptomyces rimosus, Streptomyces roseochromogenus, Streptomyces sp., Aspergillus ochraceus, Paecilomyces carneus, Penicillium notatum, Candida humicola, Rhodotorula ruba, Rhodotorula glutinis, Saccharomyces cerevisiae, Torulopsis aeria, Torulopsis magnoliae* or *Torulopsis rotundata*.

5. A process according to claim 1, wherein the reaction is carried out with a microorganism selected from *Streptomyces griseus* NRRL 15727, *Streptomyces roseochromogenus* ATCC 13400, Streptomyces sp. NRRL 15728, *Streptomyces hydrogenans* ATCC 19631, *Candida humicola* NRRL Y-1266, *Rhodotorula glutinis* NRRL Y-15726 or a mutant thereof.

6. A process according to claim 1, wherein the reaction is carried out with a compound of formula II in which $R^2$ is selected from the group consisting of methyl, ethyl or t-butyl.

7. A process according to claim 1, wherein the reaction is carried out with a compound of formula II in which $R^1$ is methyl or phenyl.

8. A process according to claim 1, wherein the reaction is carried out at a pH-value of 3 to 8.

9. A process according to claim 1, wherein the reaction is carried out at a temperature of 20° C. to 35° C.

* * * * *